United States Patent [19]

Kumakura et al.

[11] Patent Number: 5,390,667
[45] Date of Patent: Feb. 21, 1995

[54] ABSORPTION OF CARBON DIOXIDE GAS CONTAINED IN EXHALATION OF INHALATION ANESTHETIC SUBJECT

[75] Inventors: Manami Kumakura; Toshikazu Kawai, both of Saitama, Japan

[73] Assignee: Central Glass Company, Limited, Yamaguchi, Japan

[21] Appl. No.: 937,771

[22] Filed: Sep. 1, 1992

[30] Foreign Application Priority Data

Sep. 3, 1991 [JP] Japan .................................. 3-222567

[51] Int. Cl.$^6$ ................................................ A62B 7/10
[52] U.S. Cl. ............................ 128/205.12; 128/203.12
[58] Field of Search ...................... 128/205.27, 205.28, 128/205.12, 201.25, 202.26, 203.12

[56] References Cited

U.S. PATENT DOCUMENTS 3,489,693  1/1970  Bovard ................................ 502/400
3,557,011  1/1971  Colombo et al. .................... 252/189
3,923,057  12/1975  Chalon ............................ 128/203.16

*Primary Examiner*—Edgar S. Burr
*Assistant Examiner*—Aaron J. Lewis
*Attorney, Agent, or Firm*—Keck, Mahin & Cate

[57] ABSTRACT

Concerning the recirculation of an inhalation anesthetic in a closed or semiclosed anesthetic system, the object of the invention is removing carbon dioxide gas from the exhalation of the patient under inhalation anesthesia by using an absorbent which hardly causes decomposition of the anesthetic remaining in the exhalation. The object is accomplished by using a magnesium compound such as magnesium oxide, magnesium hydroxide or magnesium hydroxycarbonate as the principal material of the absorbent to absorb carbon dioxide gas. It is preferred to use magnesium hydroxide with addition of a small amount of water.

9 Claims, No Drawings

ABSORPTION OF CARBON DIOXIDE GAS CONTAINED IN EXHALATION OF INHALATION ANESTHETIC SUBJECT

BACKGROUND OF THE INVENTION

This invention relates to inhalation anesthesia using a closed or semiclosed anesthetic system, and more particularly to the removal of carbon dioxide gas from the exhalation of the anesthetic subject by using an absorbent.

Inhalation anesthesia is a predominant means of a general anesthesia for a surgical operation because inhalation anesthesia has advantages over intravenous anesthesia such as smallness of danger, ease of controlling the depth of anesthesia and earliness of recovery from anesthesia after the operation.

In inhalation anesthesia a portion of the inhaled anesthetic is not metabolized in the body of the patient and remains in the exhalation of the patient. Usually a closed or semiclosed anesthetic system is used to recirculate the exhaled anesthetic with addition of the anesthetic to make up the depletion by the intake in the body.

For the recirculation of the exhaled anesthetic it is necessary to remove carbon dioxide gas contained in the exhalation. Usually an absorbent is used for this purpose, and conventional absorbents for this purpose use calcium hydroxide as the principal material sometimes with the addition of a small amount of an auxiliary component such as barium hydroxide, sodium hydroxide, potassium hydroxide and/or silica. Although any of these conventional absorbents is high in the ability to absorb carbon dioxide gas, there is a possibility that the absorbent adsorbs and decomposes a fraction of the anesthetic coexisting with carbon dioxide gas.

In fact, experiments have evidenced partial decomposition of some widely used inhalation anesthetic by contact with a conventional absorbent for carbon dioxide gas using calcium hydroxide as the principal material. For example, when an experimental exhalation gas containing 2-bromo-2-chloro-1,1,1-trifluoroethane (a widely used inhalation anesthetic, called halothane) and carbon dioxide gas is brought into contact with an absorbent using calcium hydroxide as the principal material in a glass vial, a fraction of halothane is decomposed to form 1,1-difluoro-2-bromo-2-chloroethylene and some other unsaturated compounds. In the case of the contact of fluoromethyl-1,1,1,3,3,3-hexafluoro-2-propyl ether (another widely used inhalation anesthetic, called sevoflurane) with calcium hydroxide, a fraction of sevoflurane is decomposed to form 1,1,3,3,3-pentafluoro-2-(fluoromethoxy)-1-propene and/or 1,1,1,3,3-pentafluoro-2-(fluoromethyl)-3-methoxypropane.

It is uncertain whether the above identified decomposition products are harmful or not, and it will take great efforts to clarify the effects of these compounds on the human body. Of course it is undesirable that an inhalation anesthetic contains some substances that have a doubt about pharmacological safety, and even if such a doubt is groundless it is desirable to prevent intrusion of unnecessary substances into an inhalation anesthetic.

SUMMARY OF THE INVENTION

The present invention relates to the removal of carbon dioxide gas from the exhalation of a patient who is under inhalation anesthesia using a closed or semiclosed anesthetic system to recirculate the anesthetic remaining in the exhalation gas, and it is an object of the invention to accomplish the removal of carbon dioxide gas by using a new absorbent which efficiently absorbs carbon dioxide gas and hardly decomposes the anesthetic.

According to the invention the above object is accomplished by using a magnesium compound as the principal material of the absorbent for the absorption of the carbon dioxide gas.

Magnesium compounds such as magnesium oxide, magnesium hydroxide and magnesium hydroxycarbonate can absorb carbon dixoide gas, though these magnesium compounds are somewhat weaker than calcium hydroxide in the power of absorbing carbon dioxide. Unexpectedly we have discovered that in the case of using a magnesium compound as the absorbent the inhalation anesthetic coexisting with carbon dioxide gas is hardly decomposed.

In this invention a preferred magnesium compound is magnesium hydroxide. There is no question about the safety of magnesium hydroxide to the human body. In fact magnesium hydroxide has been used in some pharmaceuticals such as antacids and cathartics. It is suitable to use magnesium hydroxide with addition of a small qunatity of water.

The present invention is applicable to various inhalation anesthetics including volatile anesthetics such as, for example, halothane, sevoflurane, 1-chloro-2,2,2-trifluoroethyldifluoromethyl ether (called isoflurane), 2-chloro-1,1,2-trifluoroethyldifluoromethyl ether (called enflurane), diethyl ether and 1,2,2,2-tetrafluoroethyldifluoromethyl ether (called desflurane) and gaseous anesthetics such as, for example, nitrous oxide and 1,1-dichloro-2,2-difluoroethylmethyl ether (called methoxyflurane).

DESCRIPTION OF THE PREFERRED EMBODIMENTS

As the principal material of an absorbent according to the invention it is possible to use any of magnesium oxide, magnesium hydroxide and magnesium hydroxycarbonate and any combination of these magnesium compounds.

It is preferable to use magnesium hydroxide by adding at least 1 part by weight of water to 100 parts by weight of magnesium hydroxide. When the amount of addition of water is less than 1 wt % the absorbent is low in the rate of absorbing carbon dioxide gas so that a relatively large quantity of magnesium hydroxide must be used to absorb a given quantity of carbon dioxide. There is no strict upper limit to the amount of water. However, in practice it is necessary to maintain the absorbent in a suitable form, and therefore it is suitable to mix not more than 100 parts by weight of water with 100 parts by weight of magnesium hydroxide.

In the case of using magnesium oxide it is not necessary to add water.

An absorbent according to the invention can be used in various forms according to the type of the employed inhalation anesthetic system. For example, the absorbent may be in the form of powder, granules, pellets or tablets.

The following nonlimitative examples are illustrative of the invention.

EXAMPLE 1

In a 125 ml vial, 21 g of a fine powder of magnesium hydroxide of reagent grade was well mixed with 4 ml of ion-exchanged water (20 wt % of magnesium hydroxide). The septum and cap of the vial were airtightly closed with a crimper, and the air was expelled from the vial by operating an aspirator for 1 min. Then 20 $\mu l$ of sevoflurane was introduced into the vial so as to run on the vial wall surface and vaporize. Next, air containing 0.07 vol % of carbon dioxide was introduced into the vial with a syringe needle stabbed into the septum until the atmospheric pressure was resumed in the vial. After that the vial was kept in a constant-temperature oven maintained at 37° C., and 2.5 ml of carbon dioxide gas was repeatedly injected into the vial at regular intervals of 10 min.

After the lapse of 0.5 h, 3 hr and 6 h from the addition of sevoflurane, and while a solid-gas equilibrium has been reached in the vial, the gas phase in the vial was sampled and analyzed by head space gas chromatography to determine the concentration of sevoflurane and concentrations of 1,1,3,3,3-pentafluoro-2-(fluoromethoxy)-1-propene (referred to as Compound A) and 1,1,1,3,3-pentafluoro-2-(fluoromethyl)-3-methoxypropane (referred to as Compound B) which might be formed by decomposition of sevoflurane. The sampling time was always 1 min. In this example, and also in the subsequent examples, the gas chromatograph was Model GC-380 (with cooling system) of GL Science Co., and the particulars of the gas chromatography were as follows.

Column: J & W, DB-WAX, 30 m–0.53 mm
Injection temperature: 170° C.
Column temperature: 20°–50° C.
Initial hold time: 5 min
Rate of temperature rise: 10° C./min
Detector: FID
Detection temperature: 170° C.
Splitless time: 30 sec
Carrier gas: He
Column head pressure: 0.3 kg/cm$^2$ With this gas chromatograph the lower limit of detection of either Compound A or Compound B was 0.1 ppm by volume.

The gas chromatography analysis revealed that there was little change in the concentration of sevoflurane with the lapse of time. Neither Compound A nor Compound B could be detected at any sampling point, even after the lapse of 6 hr from the addition of sevoflurane. After the lapse of 24 h the weight of magnesium hydroxide in the vial was measured to find an increase by 0.424 g. By calculation from this weight increase, the magnesium hydroxide had absorbed about 60% of carbon dioxide gas injected into the vial.

EXAMPLE 2

The testing process of Example 1 was repeated except that the quantity of ion-exchanged water water was increased to 6 ml (30 wt % of magnesium hydroxide).

In this example too there was little change in the concentration of sevoflurane with the lapse of time. Neither Compound A nor Compound B could be detected at any sampling point, even after the lapse of 8 hr from the addition of sevoflurane. In 24 h the weight of magnesium hydroxide in the vial increased by 0.495 g, which was attributed to the absorption of about 70% of carbon dioxide gas injected into the vial.

Comparative Example 1

The testing process of Example 1 was modified only in the following points.

In place of magnesium hydroxide in Example 1, 26 g of a commercial absorbent for carbon dioxide, SODA-SORB of W. R. GRACE & Co., was used without adding water. The principal and major material of this absorbent was calcium hydroxide. Considering the change of absorbents, the quantity of the periodically added (at intervals of 10 min) carbon dioxide gas was increased from 2.5 ml in Example 1 to 3.5 ml.

In this case the concentration of sevoflurane greatly lowered with the lapse of time. The initial concentration of sevoflurane was 3.0 vol %, but in 6 h the concentration lowered to 0.4 vol %. At the first sampling point (after 0.5 h) the sampled gas contained 194 ppm (by volume) of Compound A, though Compound B could not be detected. At the second sampling point (after 3 h) the gas contained 10 ppm (by volume) of Compound B, though Compound A could not be detected. At the third sampling point (after 6 h) the gas contained 16 ppm (by volume) of Compound B, though Compound A could not be detected.

In 24 h the weight of the absorbent in the vial increased by 0.832 g, which indicated the absorption of about 80% of carbon dioxide gas injected into the vial.

EXAMPLE 3

The testing process of Example 1 was repeated except that 16 $\mu l$ of halothane was used in place of 20 $\mu l$ of sevoflurane in Example 1.

There was little change in the concentration of halothane with the lapse of time, even after the lapse of 24 h.

Possible decomposition products of halothane were 1,1-difluoro-2-bromo-2-chloroethylene (referred to as Compound C) and 2-chloro-1,1,1-trifluoroethane (referred to as Compound D). With the gas chromatograph used for analysis the lower limit of detection of either Compound C or Compound D was 0.1 ppm by volume. At the first sampling point (after 0.5 h) neither Compound C nor Compound D could be detected. At the second sampling point (after 3 h) the total concentration of Compounds C and D was 8 ppm by volume, and at the third sampling point (after 6 h) the total concentration of Compounds C and D was 12 ppm by volume.

In 24 h, the weight of magnesium hyroxide in the vial increased by 0.430 g, which was attributed to the absorption of about 60% of carbon dioxide gas injected into the vial.

Comparative Example 2

The testing process of Comparative Example 1 was repeated except that 16 $\mu l$ of halothane was used in place of 20 $\mu l$ of sevoflurane.

In this case there was a slight decrease in the concentration of halothane with the lapse of time. The initial concentration of halothane was 3.0 vol %, but after the lapse of 24 h the concentration was 2.8 vol %. The sampled gases contained both Compound C and Compound D in higher concentrations than in Example 3. That is, the total concentration of Compounds C and D was 20 ppm by volume after the lapse of 0.5 h, 40 ppm after the lapse of 3 h and 27 ppm after the lapse of 6 h.

What is claimed is:

1. A method of removing carbon dioxide gas from exhalation of a patient who is under inhalation anesthesia, consisting of the steps of administering to a patient, in a closed or semiclosed anesthetic system an inhalation anesthetic which is a compound having first and second carbon atoms which are adjacent to each other, said first carbon atom being bonded to at least one halogen atom, said second carbon atom being bonded to at least one hydrogen atom, and bringing exhalation of the patient into contact with an absorbent which absorbs carbon dioxide gas, characterized in that a magnesium compound is used as the principal material of said absorbent, and the inhalation anesthetic remains substantially undecomposed during absorption.

2. A method according to claim 1, wherein said magnesium compound is selected from the group consisting of magnesium oxide, magnesium hydroxide and magnesium hydroxycarbonate.

3. A method according to claim 1, wherein said magnesium compound is magnesium hydroxide, said absorbent comprising water which amounts to at least 1 wt % of said magnesium hydroxide.

4. A method according to claim 3, wherein the amount of said water is not more than 100 wt % of said magnesium hydroxide.

5. A method according to claim 1, wherein said absorbent is in the form of a powder.

6. A method according to claim 1, wherein said absorbent is in a granular form.

7. A method according to claim 1, wherein said absorbent is in the form of pellets or tablets.

8. A method according to claim 1, wherein said inhalation anesthetic is selected from the group consisting of 2-bromo-2-chloro-1,1,1-trifluoroethane, fluoromethyl-1,1,1,3,3,3-hexafluoro-2-propyl ether, 1-chloro-2,2,2-trifluoroethyldifluoromethyl ether, 2-chloro-1,1,2-trifluoroethyldifluoromethyl ether, 1,2,2,2-tetrafluoroethyldifluoromethyl ether and 1,1-dichloro-2,2-difluoroethylmethyl ether.

9. A method according to claim 1, wherein said inhalation anesthetic is selected from the group consisting of 2-bromo-2-chloro-1,1,1-trifluoroethane and fluoromethyl-1,1,1,3,3,3-hexafluoro-2-propyl ether.

* * * * *